United States Patent [19]

Wilson et al.

[11] 4,335,212

[45] Jun. 15, 1982

[54] FERMENTATION PROCESS FOR (5R,6S,8S)-3-(2-AMINOETHYLTHIO)-6-(1-HYDROXYETHYL)-7-OXO-1-AZABICYCLO[3.2.0]HEPT-2-ENE-2-CARBOXYLIC ACID

[75] Inventors: Kenneth E. Wilson, Westfield, N.J.; August J. Kempf, Staten Island, N.Y.

[73] Assignee: Merck & Co., Inc., Rahway, N.J.

[21] Appl. No.: 274,702

[22] Filed: Jun. 17, 1981

[51] Int. Cl.$^3$ .................... C12P 17/18; C12P 17/10
[52] U.S. Cl. .................................... 435/119; 435/121
[58] Field of Search ........................... 435/119, 121

[56] References Cited

U.S. PATENT DOCUMENTS

| | | | |
|---|---|---|---|
| 4,247,640 | 1/1981 | Kempf et al. | 435/119 |
| 4,304,867 | 12/1981 | Kahan et al. | 435/253 |

*Primary Examiner*—Lionel M. Shapiro
*Attorney, Agent, or Firm*—Frank M. Mahon; Hesna J. Pfeiffer; James A. Arno

[57] ABSTRACT

Disclosed is a fermentation process for preparing and isolating the antibiotic, (5R,6S,8S)-3-(2-aminoethylthio)-6-(1-hydroxyethyl)-7-oxo-1-azabicyclo[3.2.0]hept-2-ene-2-carboxylic acid in substantially pure form.

2 Claims, No Drawings

FERMENTATION PROCESS FOR (5R,6S,8S)-3-(2-AMINOETHYLTHIO)-6-(1-HYDROXYETHYL)-7-OXO-1-AZABICYCLO[3.2.0]HEPT-2-ENE-2-CARBOXYLIC ACID

BACKGROUND OF THE INVENTION

This invention relates to a fermentation process for preparing (5R,6S,8S)-3-(2-aminoethylthio)-6-(1-hydroxyethyl)-7-oxo-1-azabicyclo[3.2.0]hept-2-ene-2-carboxylic acid (I) which is useful as an antibiotic:

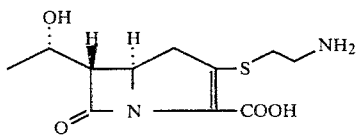

The antibiotic of Structure I will be recognized as 8-epi-thienamycin (also known as desacetyl 890 $A_3$). Thienamycin (II) is disclosed and claimed in U.S. Pat. No. 3,950,357 (Apr. 13, 1976):

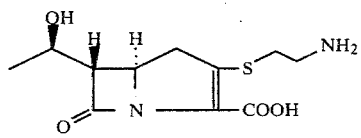

This patent disclosing and claiming thienamycin is incorporated herein by reference since 8-epi-thienamycin (I) is isolated from the very same fermentation broths that yield thienamycin and co-produced antibiotic, northienamycin, as described in commonly assigned U.S. Pat. No. 4,247,640, issued Jan. 27, 1981.

The compound of structure I is fully disclosed and claimed in commonly assigned U.S. Pat. No. 4,234,596 issued Nov. 18, 1980. To the extent that the cited commonly assigned U.S. Pat. No. 4,234,596 describes the antibiotic utility of I, it is incorporated herein by reference.

DETAILED DESCRIPTION OF THE INVENTION

Incorporated by reference U.S. Pat. No. 3,950,357 fully describes the fermentation procedures involving the novel microorganism *Streptomyces cattleya*. It is from these fermentation broths that the compound of Structure I was unexpectedly found. The following example describes the basic fermentation process and the isolation procedures utilized in isolating the antibiotic I in substantially pure form.

EXAMPLE 1

A tube of lyophilized culture of *Streptomyces cattleya* is opened aseptically and the contents suspended in 50 ml of sterile Medium A contained in a 250 ml baffled Erlenmeyer flask. Medium A has the following composition:

| Medium A | |
|---|---|
| Yeast Autolysate (Ardamine*) | 10.0 g |
| Glucose | 10.0 g |
| Phosphate Buffer** | 2.0 ml |
| MgSO$_4$7H$_2$O | 0.05 g |
| Distilled H$_2$O | 1000 ml |
| pH: adjust to 6.5 using NaOH | |

*Ardamine: Yeast Products Corporation
**Phosphate Buffer Solution

| | |
|---|---|
| KH$_2$PO$_4$ | 91.0 g |
| NaHPO$_4$ | 95.0 g |
| Distilled H$_2$O | 1000 ml |

The inoculated flask is shaken at 28° C. on 220 rpm shaker (2 inches throw) for 48 hours. A portion (40 ml.) of the 48-hour broth is removed aseptically and mixed with 40 ml. of aqueous, sterile 20% (v/v) glycerol. Aliquot quantities (2.0 ml.) of the resulting mixture are pipetted into sterile 1 dram vials which are then frozen and stored in the vapor phase of a liquid nitrogen freezer.

Frozen vial contents are used to inoculate a 250 ml. baffled Erlenmeyer flask containing 50 ml. of Medium A. This seed flask is shaken at 28° C. on a 160 rpm shaker at 28° C. for 24 hours.

Portions (10.0 ml.) from this seed flask are used to inoculate 2-liter baffled Erlenmeyer flasks containing 500 ml. of Medium A. These seed flasks are shaken on a 160 rpm shaker at 28° C. for 24 hours.

A portion (1.0 L) of the pooled contents of these seed flasks is used to inoculate a 756 liter stainless steel fermentor containing 467 liters of Medium A. This tank is operated at 28° C. using an agitation rate of 130 rpm and an airflow of 10 cu. ft. per minute for 24 hours. Polyglycol 2000 (Dow Chemical Corp.) is used as required as a defoamer but not to exceed 0.1%. Measurements of pH and dextrose are made and are as follows:

| Age (Hours) | 0 | 12 | 14 |
|---|---|---|---|
| pH | 6.4 | 6.4 | 6.6 |
| Dextrose mg/ml 6 | 8.1 | 8.1 | 8.1 |

A portion (453 L) of this growth is used to inoculate a 5670 liter stainless steel fermentor containing 4082 liters of Medium E, wherein Medium E has the composition:

| Medium E | |
|---|---|
| Cerelose | 25.0 g |
| Corn Steep Liquor (wet basis) | 15.0 g |
| Distiller's Solubles | 10.0 g |
| Cottonseed Media (pharmamedia) | 5.0 g |
| CoCl$_2$ · 6H$_2$O | 0.01 g |
| CaCO$_3$ (after pH adjustment) | 3.0 g |
| Polyglycol 2000 | 0.25% |
| Tap water | 1000 ml | pH: adjust to 7.3 using NaOH

This tank is operated at 24° C. using an agitation rate of 70 rpm and an airflow of 54.3 cu. ft. per minute for 144 hours. Defoamer, polyglycol 2000, is added as required but does not exceed 0.1%. Assays are performed using the supernatant of centrifuged broth. Assays are run by the disc-diffusion procedure using ⅝-inch filter-paper discs and 10 ml. assay plates and the results tabulated in the table below under the heading "Antibiotic Activity (10 ml. plates)." The 10 ml. assay plates are prepared as follows: An overnight growth of the assay organism, *Staphylococcus aureus* ATCC 6538P, in nutrient broth plus 0.2% yeast extract is diluted with nutrient broth plus 0.2% yeast extract to a suspension having 40% transmittance at a wavelength of 660 nm. This suspension is added to Difco nutrient agar supplemented with 2.0 g/l Difco yeast extract, at 47° C. to 48° C., to make a composition containing 33.2 ml. of the suspension per liter of agar. A portion (10 ml.) of this suspension is poured into petri plates of 85 mm. diameter, and the plates are chilled and held at 4° C. until used (5 day maximum).

| Age | pH | Dextrose mg/ml | Antibiotic Activity (10 ml. plates) Zone Diameter (mm) |
|---|---|---|---|
| 0 | 6.6 | 22.2 | |
| 12 | 6.3 | 20.2 | |
| 24 | 5.8 | 18.0 | 0 |
| 36 | 6.0 | 13.2 | 21.5 |
| 48 | 6.0 | 8.6 | 21.5 |
| 60 | 5.7 | 6.4 | 26.5 |
| 72 | 5.8 | 2.7 | 25.5 |
| 84 | 6.2 | 0.3 | 27.5 |
| 96 | 6.4 | 0.2 | 36.0 |
| 108 | 6.4 | 0 | 35.0 |
| 120 | 6.3 | | 37.0 |
| 132 | 5.8 | | 37.5 |
| 144 | 5.9 | | 37.5 |

The 4,258 liters of fermentation broth is cooled to 15° C. and filtered using a 30 inch filter press and 204 kg. of filter aid admix. The filter press and mycelial cake are washed with sufficient cold deionized water to bring the filtered broth to the original volume. The filtered broth is cooled to 0°–5° C. and adjusted to pH 6.8–7.2. A 38 gram amount of (ethylenedinitrilo)tetraacetic acid, disodium salt (EDTA) is added to the filtrate. Two columns, each containing 416 L of Dowex 1×2 resin, 50–100 mesh on the bicarbonate cycle, are cooled by washing each column with 750 L of deionized water at 0°–5° C. Approximately one-half of the cooled filtered broth, adjusted to pH 7.2–7.3, is adsorbed on each column at about 45 L/min. Each column is then washed with 750 L of deionized water at 0°–5° C. at the same flow rate and eluted with carbon dioxide-saturated, deionized water at 2° C. and 23 L/min. Three fractions of 750 L, 720 L, and 190 L are collected. The second fractions of each column are combined and concentrated to 9.2 L by reverse osmosis at about 10° C. and pH 4.9–5.4.

The 9.2 L concentrate, pH 5.5–6.0, is chromatographed on 83 L of Dowex 1×2, 50–100 mesh, chloride cycle resin at 1.9 L/min. in deionized water (0°–5° C.). Eighteen fractions are collected. Fraction one is 60 L and the remainder are 8 L each. Each fraction is adjusted to pH 6.2–6.4 with concentrated ammonia and assayed. Fractions 4–10 are combined and concentrated at 10° C. to 6.5 L by reverse osmosis. The pH of the concentrate is 6.8.

Six liters of concentrate then are chromatographed on 83 L of Amberlite XAD-2, 20–50 mesh, resin precooled to 7° C. The column is eluted with deionized water (0° to 5° C.) at 1.9 L/min. Sixteen fractions are collected. Fractions 1 and 16 are 79 L each and Fractions 2 through 15 are 12 L each. Fractions 5 through 15 are combined and further worked up to afford thienamycin. Fraction 16 is processed as described below to afford essentially pure 8-epi-thienamycin.

Fraction 16 from the XAD-2 chromatography described above was concentrated and lyophilized. A 7.0 mg sample of the lyophilized product was dissolved in 0.1 ml. of 0.01 M sodium phosphate/0.025 mM EDTA, pH 7.0, and chromatographed in the same solvent at 0.2 ml/min. on a 4 ml column (0.46 cm ID×24 cm) of Bio-Rad Aminex 5-A resin, sodium cycle. Column effluent was monitored by UV at 335 nm. Thienamycin eluted at 1.9 column volumes. Effluent from 2.1 column volumes to 2.47 column volumes was collected as the 8-epi-thienamycin rich-cut. Five further 7 mg samples of the lyophilized product were similarly chromatographed. The combined rich cut from all runs contained 0.45 mg of 8-epi-thienamycin and 0.55 mg of thienamycin by UV and HPLC assay (sample A).

A 15 mg sample of the lyophilized product was dissolved in 0.20 ml of 0.01 M sodium phosphate/0.025 mM EDTA (pH 6.9) and chromatographed in the same solvent on an 8 ml column (0.65 cm ID×24 cm) of Bio-Rad Aminex A-5 resin, sodium cycle. The flow rate was 0.40 ml/min. and the column effluent was monitored by UV at 325 nm. Effluent from 1.9 column volumes to 2.3 column volumes was collected as the 8-epi-thienamycin rich-cut. Eight additional 15 mg samples of the lyophilized product were purified analogously. The combined rich-cut of all nine runs was concentrated to 31 ml. Four 7.5 ml aliquots of the concentrate each were further concentrated to 150 to 200 mcl and rechromatographed on 8 ml of Bio-Rad Aminex A-5 resin as described above. Three fractions were collected and corresponding fractions pooled for the four runs. The 8-epi-thienamycin was primarily in Fraction 2 (effluent from 1.98–2.05 column volumes—0.44 mg 8-epi-thienamycin) and Fraction 3 (effluent from 2.05–2.64 column volumes—0.67 mg 8-epi-thienamycin).

Sample A, above, and Fraction 2, above, were combined, concentrated to 320 mcl and chromatographed on 8 ml of Bio-Rad Aminex A-5 resin as described above. The effluent from 1.91 to 2.3 column volumes was collected, combined with Fraction 3, above, concentrated to 350 mcl and chromatographed on 8 ml of Bio-Rad Aminex A-5 resin as described above. Eluate between 1.95 and 2.39 column volumes of total effluent was collected as the 8-epi-thienamycin rich-cut. The rich-cut was concentrated to 1 ml and chromatographed on 21 ml of pulverized Amberlite XAD-2 resin, −400 mesh (Rohm and Haas). The eluting solvent was distilled, deionized water and the flow rate was 1 ml/min. One-ml fractions were collected and assayed by HPLC (Waters $C_{18}$ μ-Bondapak) at 275 nm. Fractions 27–44 were combined as essentially pure 8-epi-thienamycin (0.63 mg). The rich cut was concentrated to 1 ml and lyophilized to a fluffy white solid.

The subject matter which applicants regard as their invention is particularly pointed out and distinctly claimed as follows.

What is claimed is:

1. A process for preparing 8-epi-thienamycin having the structure:

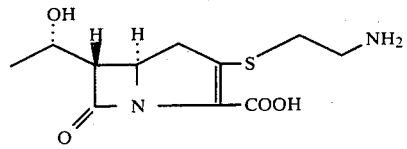

which comprises cultivating a thienamycin-producing strain of *Streptomyces cattleya* in an aqueous nutrient medium containing assimilable sources of carbohydrate, nitrogen and inorganic salts under submerged aerobic conditions and recovering the 8-epi-thienamycin so produced in substantially pure form.

2. The process of claim 1 wherein the organism cultivated is *Streptomyces cattleya* NRRL 8057.

* * * * *